United States Patent [19]

Franz et al.

[11] 4,268,448
[45] May 19, 1981

[54] PROCESS FOR THE PRODUCTION OF MALEIC ANHYDRIDE

[75] Inventors: Gerhard Franz; Franz Nierlich; Hans-Josef Ratajczak, all of Marl, Fed. Rep. of Germany

[73] Assignee: Chemische Werke Huls Aktiengesellschaft, Marl, Fed. Rep. of Germany

[21] Appl. No.: 114,448

[22] Filed: Jan. 22, 1980

[30] Foreign Application Priority Data

Jan. 26, 1979 [DE] Fed. Rep. of Germany ....... 2902986

[51] Int. Cl.³ ........................................... C07D 307/60
[52] U.S. Cl. .............................. 260/346.75; 252/437; 252/454
[58] Field of Search .................................. 260/346.75

[56] References Cited

U.S. PATENT DOCUMENTS 4,021,427  5/1977  Dolhyj et al. ................. 260/346.75

Primary Examiner—Henry R. Jiles
Assistant Examiner—Bernard Dentz
Attorney, Agent, or Firm—Millen & White

[57] ABSTRACT

Ethylenically unsaturated $C_4$-n-hydrocarbons are oxidized to maleic anhydride by passing a stream of oxygen-containing gas at high temperature over a catalyst of the formula $$W_a Mo_b Sb_c Y_d X_e O_x$$

wherein $Y=P$, Si; $X=V$, Bi, Te, alkali metal; a and b each $=1-12$; $c=2-20$; $d=0.2-2$; $e=0-10$; and x is the number of oxygen atoms required to satisfy the remaining valences of the other elements, prepared by reacting an Sb compound and optionally also a V, Bi, Te and/or alkali metal compound, with a solution of a heteropoly acid of Mo and W, drying and tempering the resultant blue complex.

6 Claims, No Drawings

PROCESS FOR THE PRODUCTION OF MALEIC ANHYDRIDE

BACKGROUND OF THE INVENTION

This invention relates to a novel process for the production of maleic anhydride by the catalyzed high temperature oxidation of unsaturated $C_4$-hydrocarbons.

Maleic anhydride can be produced by the oxidation of a saturated or unsaturated $C_4$-hydrocarbon in the presence of a suitable catalyst. The conventional methods which use vanadium-phosphorus catalysts have the disadvantage that the resultant yields of maleic anhydride are too low. See U.S. Pat. Nos. 3,474,041 and 3,618,959. In addition, vanadium-phosphorus catalysts have only a short contact lifetime since the selectivity is markedly reduced by the discharge of phosphoric acid and by the reoxidation of tetravalent vanadium. By the continuous or discontinuous metered feeding of volatile phosphorus compounds into the process gas stream, the lifetime can be only inadequately prolonged.

In U.S. Pat. No. 4,021,427, molybdenum-antimony catalysts are described as useful for the oxidation of butadiene. These catalysts are prepared by heating a slurry of the starting compounds. By the addition of a metallic component a partial reduction of the hexavalent molybdenum is to be achieved. However, processes which employ these catalysts are unsatisfactory with respect to the reproducibility of the catalyst preparation and the selectivity with respect to maleic anhydride.

It is an object of the present invention to provide a novel process for the catalyzed oxidation of unsaturated n-$C_4$-hydrocarbons to maleic anhydride employing a catalyst which can be prepared in a reproducible fashion, has a long lifetime, and produces maleic anhydride with very high selectivity.

SUMMARY OF THE INVENTION

The catalysts employed in the process of this invention have the formula

$$W_aMo_bSb_cY_dX_eO_x$$

wherein Y represents phosphorus and/or silicon; X is one or more of vanadium, bismuth, tellurium and an alkali metal; a and b are integers from 1 to 12; c is an integer from 2 to 20; d is an integer from 0.2 to 2; e is an integer from 0 to 10; and x is the number of oxygen atoms required to satisfy the remaining valences of the other elements.

These catalysts are obtained by combining a compound of trivalent antimony and optionally a vanadium, bismuth, tellurium and/or alkali compound, with a homogenous solution of the heteropoly acids of molybdenum and tungsten at a temperature of 0°–200° C.; drying; and then tempering at a temperature of 300°–500° C. Upon the addition of trivalent antimony to a homogeneous solution of the heteropoly acids of molybdenum and of tungsten, a deep-blue catalyst complex is formed which, after removing the solvent, calcining and shaping, can be utilized directly in the oxidation process.

In the process of this invention, a mixture of ethylenically unsaturated n-$C_4$-hydrocarbons and an oxygen-containing gas at an elevated temperature are brought into contact with a thus-produced catalyst.

DETAILED DISCUSSION

Preferred catalysts of this invention are those of the above formula wherein:

(a) Y is P;
(b) a is an integer from 1 to 12, especially those of (a), above;
(c) b is an integer from 1 to 2, especially those of each of (a) and (b), above;
(d) c is an integer from 2 to 20, especially those of each of (a) to (c), above;
(e) d is an integer from 0.2 to 2, especially those of each of (a) to (d), above;
(f) e is an integer from 0 to 10, especially those of each of (a) to (e), above;
(g) when e is an integer greater than 0, X is one or both of V and Cs, especially those of each of (a) to (f), above.

In the preparation of a catalyst of this invention, the use of heteropoly acids of molybdenum and tungsten in combination with trivalent antimony compounds is essential. These heteropoly acids are clearly defined, reproducible compounds distinguished by a very high solubility in water and many oxygen-containing organic solvents. Additionally, the heavy metals in the heteropoly acids are present in a redox-labile form.

Upon the addition of a compound of trivalent antimony to the solution of a molybdenum heteropoly acid, a deep-blue gel is formed. This behavior can be traced back to the partial reduction of the hexavalent molybdenum by the trivalent antimony. Merely drying and calcining such a gel yields a good catalyst. However, distinctly superior catalysts are obtained by utilizing, instead of a solution of the pure molybdenum heteropoly acid, a solution of a mixture of the heteropoly acids of molybdenum and tungsten, and adding thereto a compound of trivalent antimony. This is a synergistic effect because completely unsatisfactory results are obtained with the tungsten heteropoly acids of antimony alone. The additional presence of vanadium, bismuth, tellurium and/or an alkali can also be advantageous.

Preferred heteropoly acids of molybdenum and tungsten are those with phosphorus or silicon as the hetero atom. Examples of such heteropoly acids are: $H_3[PMo_{12}O_{40}]$; $H_{12}[P_2Mo_{18}O_{65}]$; $H_3[PW_{12}O_{40}]$; $H_3[PW_2Mo_{10}O_{40}]$; $H_3[PW_6Mo_6O_{40}]$; $H_8[SiW_{12}O_{42}]$; $H_8[SiMo_{12}O_{42}]$.

The heteropoly acids are prepared, for example, in accordance with the methods known from the literature: 1. Drechsel ether method; E. Dreschel, Chem. Ber. 20, 1952 (1887); 2. double reaction with salts; 3. heating of the corresponding oxides (optionally under pressure) in water.

The trivalent antimony can be utilized in any desired form, preferably as the halogenide or oxide.

The compounds of vanadium, bismuth, tellurium and/or the alkali metals preferably are nitrates or oxides.

In the production of the catalysts, a homogeneous solution of the heteropoly acids is ordinarily prepared first. Suitable solvents are water and oxygen-containing organic compounds, e.g., ethanol and isopropanol. With vigorous agitation, a compound of trivalent antimony is added to this solution, either in incremental portions or all at once. However, without any adverse effect on the quality of the catalyst, it is also possible to add the heteropoly acid or a mixture of such acids to a solution or suspension of a trivalent antimony compound.

The element or elements of group X can be added to the reaction mixture at any desired point in time.

The temperature of the reaction solution can vary widely, e.g., between 0° to 200° C. At high temperatures, however, the use of pressure is necessary. The preferred reaction temperatures are between 30° and 110° C.

The reaction time for the production of the catalyst can also vary widely, e.g., from a few minutes to several hours, preferably from 15 minutes to 2 hours.

The formation of the blue, gel-like catalyst precursor is essential. Although its actual structure is not known, one can assume that the trivalent antimony is present in a partially oxidized form, and the hexavalent molybdenum or tungsten is present in partially reduced form. The formation of such a precursor is critical for the very good reproducibility of the catalysts.

After the formation of the precursor, which is recognizable by its intense blue color, the solvent is removed, e.g., by evaporation or under vacuum and the residue is dried. Elevated temperatures are oridinarily employed, e.g., between 100° and 200° C. The dried material is converted to a powder, e.g., crushed with a pestle or ground, and then formed into shaped articles, e.g., pellets, rods, balls, etc. One method of producing shaped articles is by compressing the powdered material into pellets. Such processing methods frequently require the addition of a lubricant, i.e., a mold release agent, e.g., graphite, stearic acid and like materials. The shaped catalyst is then calcined, e.g., at a temperature of 300°–500° C. Preferably, the catalyst is activated at a temperature of about 400°–450° C. for about 1–4 hours in an air current.

Alternatively, the catalyst material can be calcined prior to being formed into shaped articles.

The catalyst of this invention can also be applied to a support material, e.g., titanium dioxide, aluminum oxide, clay, diatomaceous earth, and the like, utilized in amounts of from 2 to 50% by weight, based on the total weight of the finished catalyst. The support material can be added to the catalyst solution, or the catalyst solution can be poured onto the support material. Alternatively, the support can be present during the entire course of the preparation of the catalyst.

Examples of unsaturated n-C$_4$-hydrocarbons which can be employed in the process of this invention are butene-1, butene-2 and preferably butadiene, which gives the highest yields of maleic anhydride, and mixtures thereof.

Maleic anhydride is produced according to the process of this invention by contacting a mixture of an ethylenically unsaturated n-C$_4$-hydrocarbon and an oxygen-containing gas with a catalyst of this invention. Typically, a stream of the mixture is passed over the catalyst in the conventional manner. Air is satisfactory as the oxygen source. However, it is also possible to use synthetic mixtures of oxygen and one or more dilution gases, e.g., nitrogen. Oxygen-enriched air can also be employed.

The molar ratio of oxygen to the unsaturated n-C$_4$-hydrocarbon can vary from about 2:1 to about 40:1, preferably from about 4:1 to 20:1.

The oxidation is conducted at a temperature between 300° and 450° C., preferably between 330° and 420° C. Temperatures above 420° C. are less favorable because further oxidation of the thus-formed maleic anhydride occurs increasingly along with the temperature. At temperatures below 300° C., the reaction rate is unacceptable low.

The oxidation generally is conducted under a slight super-atmospheric pressure. However, it is also possible to operate under normal pressure or slight subatmospheric pressure.

The oxidation can be conducted in a solid bed or in a fluidized bed of the catalyst. When using a solid bed, tube-bundle reactors should be employed to be able to sufficiently remove the thus-liberated heat of reaction.

The apparent contact period, i.e., the period of time required for an increment of the gaseous mixture to pass through the same increment of reactor volume, can range between 0.1 and 30 seconds and preferably is about 0.2–10 seconds.

Optionally, steam can likewise be added to the gaseous mixture. Quantities ranging from 0 to 20 vol-%, based on the starting gaseous mixture, do not damage the catalyst.

The catalysts produced according to the process of this invention are distinguished by a very long lifetime. During operating-life tests conducted in a pilot plant, no loss in activity and selectivity was observed after an operating period of 2 years.

Surprisingly, no discharge of phosphorus compounds or molybdenum compounds into the reaction product was observed in the catalysts of this invention. This is very surprising, especially since the problem of phosphorus discharge is one of the greatest disadvantages associated with V-P catalysts.

Also, the catalysts utilized in accordance with the claims exhibit an extraordinarily high mechanical stability, since very little dust evolution was observed after an operating period of 2 years. This behavior suggests substantially longer than 2 years operating lifetimes.

The maleic anhydride obtained by the process of this invention is obtained in very pure form. If the product stream is passed through a cooled trap system, the maleic anhydride is precipitated in the form of white crystals. The main by-products are carbon dioxide and carbon monoxide. Acetic acid and acrylic acid are obtained in smaller amounts.

The catalysts compiled in Tables I and II were prepared in accordance with the following examples.

COMPARATIVE EXAMPLE 1

Under heating, 19.64 g. of 5(NH$_4$)$_2$O.12WO$_3$.7H$_2$O is dissolved in 1.2 l. of H$_2$O and thereafter concentrated to 400 ml. by evaporation. 33.04 g. of (NH$_4$)$_6$Mo$_7$O$_{40}$.4-H$_2$O and 2.52 g. of H$_3$PO$_4$ are added to the reaction mixture, and the latter is heated until again a clear solution is obtained. To the above solution is added 25.70 g. of Sb$_2$O$_3$ and the mixture is stirred for another 2 hours at 100° C. Thereafter the water is removed by evaporation and the residue is dried overnight at 120° C. in a drying chamber. The solid mass is pulverized and compressed into pellets with 2% graphite. The catalyst is activated prior to use for 2 hours at 430° C. in an air stream.

A 25 ml. fixed-bed glass reactor having an internal diameter of 2.0 cm. is filled with 25 ml. of the catalyst, and the reactor is heated with a saline bath of the bath temperature indicated in the tables. At this bath temperature, 1,3-butadiene and air are passed through the catalyst bed with a slight pressure head of 0.1 bar, at the apparent contact periods and at the concentrations indicated in the tables. The gaseous reaction components are added in metered amounts by way of electronic volume controllers.

COMPARATIVE EXAMPLE 2

$P_1Sb_8Mo_{12}O_x$ 40.0 g. of $H_3[PMo_{12}O_{40}]$ is dissolved in 100 ml. of water. At 50° C., 23.32 g. of $Sb_2O_3$ is added all at once under vigorous agitation. A deep-blue gel is thus obtained, which is stirred for another 2 hours at 80° C. Thereafter the water is removed by evaporation until a solid mass has been formed, and the latter is dried for 10 hours at 135° C. in a drying chamber. The cake is crushed with a pestle, combined with 2% graphite, and compressed into pellets. Prior to use, the catalyst is calcined at 430° C. in an air stream for 2 hours.

The oxidation of butadiene is conducted in accordance with the procedure of Comparative Example 1.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

$P_{1.4}Sb_{11.4}W_{4.8}Mo_{12}O_x$

At 50° C. 25.66 g. of $Sb_2O_3$ is added all at once under vigorous agitation to a solution of 31.26 g. of $H_3[PMo_{12}O_{40}]$ and 18.76 g. of $H_3[PW_{12}O_{40}]$ in 150 ml. of water. The thus-produced dark-blue gel is stirred for another 2 hours at 90° C. Thereafter the water is removed by evaporation, and the residue is dried for 5 hours at 135° C. The solid cake is crushed with a pestle, combined with 2% graphite, and compressed into tablets, which were then calcined in an air stream at up to 430° C. for 2 hours.

A 25 ml. fixed bed glass reactor having an internal diameter of 2.0 cm. is filled with 25 ml. of the catalyst, and the reactor is heated with a saline bath at the temperature shown in the tables. At this bath temperature, 1,3-butadiene is passed through the catalyst bed under a slight pressure head of 0.1 bar at the apparent contact periods and concentrations listed in the tables. The metered feeding of the gaseous reactants is effected by means of electronic volume regulators.

EXAMPLE 2

The catalyst is the same as in Example 1. The oxidation of butadiene is conducted according to the procedure of Example 1.

EXAMPLE 3

$P_{1.4}Sb_{11.4}Bi_{0.26}W_{4.8}Mo_{12}O_x$

At 50° C., 15.04 g. of $Sb_2O_3$ and 1.22 g. of $Bi(NO_3)_3.5-H_2O$ are added all at once under vigorous agitation to a solution of 18.76 g. of $H_3[PMo_{12}O_{40}]$ and 11.26 g. of $H_3[PW_{12}O_{40}]$ in 70 ml. of water. The procedure of Example 1 is thereafter followed.

EXAMPLE 4

$P_{1.4}Sb_{11.4}V_{1.1}Cs_{0.6}W_{4.8}Mo_{12}O_x$

At 70° C. 15.40 g. of $Sb_2O_3$, 0.91 g. of $V_2O_5$ and 0.98 g. of $Cs_2CO_3$ are added in several portions under vigorous stirring to a solution of 18.76 g. of $H_3[PMo_{12}O_{40}]$ and 11.26 g. of $H_3[PW_{12}O_{40}]$ in 90 ml. of water. The mixture is agitated for two hours at 90° C., thus obtaining a dark-blue, viscous mass. The latter is dried in a drying chamber for 12 hours at 135° C. and thereafter crushed with a pestle. The powder is combined with 2% graphite and compressed into tablets. The latter are calcined in an air stream for 2 hours at 430° C. The oxidation of butadiene is conducted according to the procedure of Example 1.

EXAMPLE 5

$P_{1.4}Sb_{6.5}V_{0.65}Li_{0.65}W_5Mo_{12}O_x$

At 60° C., 11.67 g. of $Sb_2O_3$, 0.73 g. of $V_2O_5$ and 0.30 g. of $Li_2CO_3$ are added in several increments with vigorous agitation to a solution of 26.04 g. of $H_3[PMo_{12}O_{40}]$ and 15.96 g. of $H_3[PW_{12}O_{40}]$ in 200 ml. of water. The process is thereafter conducted according to the procedure of Example 1.

EXAMPLE 6

$P_{1.4}Sb_{11.4}Te_{0.12}W_{4.8}Mo_{12}O_x$

At 90° C., 25.66 g. of $Sb_2O_3$ and 0.16 g. of $TeO_2$ are added all at once with vigorous agitation to a solution of 31.26 g. of $H_3[PMo_{12}O_{40}]$ and 18.76 g. of $H_3[PW_{12}O_{40}]$ in 250 ml. of $H_2O$. The process is thereafter conducted according to the procedure of Example 1.

The entire analytical process is conducted by gas chromatography. To determine the maleic anhydride concentration in the product stream, the latter is conducted via heated conduits directly through the sample loop of a suitable gas chromatograph. For evaluation, the nitrogen of the starting mixture is utilized as an internal standard. In addition, the product stream can also be collected in a trap system and analyzed by the additional weighing of a suitable standard.

The long-term tests are conducted in a 200 ml. fixed bed steel reactor likewise having an inner diameter of 2.0 cm.

The results of the tests are indicated in the tables set forth below. The conversion, the yield and the selectivity are determined according to the following formulae:

$$\text{Conversion} = \frac{\text{Mole of reacted Hydrocarbon}}{\text{Mole of Hydrocarbon in the Charge}} \times 100$$

$$\text{Yield in a Single Pass} = \frac{\text{Mole of Obtained Maleic Anhydride}}{\text{Mole of Charged Hydrocarbon}} \times 100$$

$$\text{Selectivity} = \frac{\text{Yield in One Pass}}{\text{Conversion}} \times 100$$

Comparative Example 1 shows that the use of soluble molybdenum and tungsten compounds alone is not a suitable method for preparing good catalysts. The critical factor is the use of heteropoly acids. Only these compounds are capable of reacting with the trivalent antimony in the form of a redox reaction and of forming the requisite blue complex.

Comparative Example 2 demonstrates that, in the absence of tungsten, a low-reactivity catalyst is formed which does not exhibit the desired selectivity.

Examples 1-6 show the excellent results attained by means of the process and catalyst of this invention.

By comparing Examples 1 and 2, the very high reproducibility in the catalyst production is clearly evident.

Table II gives the results of a long-term experiment.

The values show that even after 2 years there has been no loss in activity and selectivity of the catalyst. Also, a discharge of catalyst elements is not observed.

TABLE I
Oxidation of 1,3-Butadiene to Maleic Anhydride

| Catalyst Active Components | Vol-% $C_4$ | Bath Temp. (°C.) | Apparent Contact Period (sec.) | Conversion (%) | Maleic Anhydride Yield mol-% One-Time Pass | Maleic Anhydride Selectivity (mol-%) |
|---|---|---|---|---|---|---|
| Comp. Example | | | | | | |
| 1  $P_{1.4}Sb_{11.4}W_{4.8}Mo_{12}O_x$ | 1.3 | 408 | 1.4 | 77.5 | 35.6 | 45.9 |
| 2  $P_1Sb_8Mo_{12}O_x$ | 1.23 | 410 | 1.4 | 98.5 | 57.1 | 58.0 |
| Example | | | | | | |
| 1  $P_{1.4}Sb_{11.4}W_{4.8}Mo_{12}O_x$ | 1.2 | 370 | 1.3 | 100 | 74.8 | 74.8 |
| 2  $P_{1.4}Sb_{11.4}W_{4.8}Mo_{12}O_x$ | 1.2 | 370 | 1.3 | 100 | 75.3 | 75.3 |
| 3  $P_{1.4}Sb_{11.4}Bi_{0.26}W_{4.8}Mo_{12}O_x$ | 2.6 | 380 | 2.0 | 100 | 69.0 | 69.0 |
| 4  $P_{1.4}Sb_{11.4}V_{1.1}Cs_{0.6}W_{4.8}Mo_{12}O_x$ | 1.1 | 385 | 1.2 | 100 | 75.5 | 75.5 |
| 5  $P_{1.4}Sb_{6.5}V_{0.65}Li_{0.65}W_5Mo_{12}O_x$ | 2.1 | 385 | 2.1 | 100 | 71.6 | 71.6 |
| 6  $P_{1.4}Sb_{11.4}Te_{0.12}W_{4.8}Mo_{12}O_x$ | 1.2 | 380 | 1.1 | 100 | 70.4 | 70.4 |

TABLE II
Long-Term Experiment for the Oxidation of 1,3-Butadiene to Maleic Anhydride

| Catalyst Example A | Operating Period (Weeks) | Vol-% $C_4$ | Bath Temp. (°C.) | Apparent Contact Period (sec.) | Conversion (%) | Maleic Anhydride Yield mol-% One-Time Pass | Maleic Anhydride Selectivity (mol-%) |
|---|---|---|---|---|---|---|---|
| $P_{1.4}Sb_{11.4}W_{4.8}Mo_{12}O_x$ | 1 | 1.54 | 376 | 1.1 | 100 | 75.9 | 75.9 |
| $P_{1.4}Sb_{11.4}W_{4.8}Mo_{12}O_x$ | 48 | 1.57 | 377 | 1.1 | 100 | 76.1 | 76.1 |
| $P_{1.4}Sb_{11.4}W_{4.8}Mo_{12}O_x$ | 109 | 1.57 | 376 | 1.1 | 100 | 75.8 | 75.8 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the production of maleic anhydride by the high temperature catalyzed oxidation of ethylenically unsaturated n-$C_4$-hydrocarbons with an oxygen-containing gas, the improvement wherein the catalyst is a compound of the formula

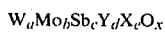

$$W_aMo_bSb_cY_dX_eO_x$$

wherein y represents phosphorus and/or silicon; X is at least one of vanadium, bismuth, tellurium and an alkali metal; a and b are integers from 1 to 12; c is an integer from 2 to 20; d is an integer from 0.2 to 2; e is an integer from 0 to 10; and x is the number of oxygen atoms required to satisfy the remaining valences of the other elements present, which catalyst is produced by mixing a compound of trivalent antimony and, when e is other than 0, at least one of a vanadium, bismuth, tellurium and alkali metal compound, with a solution of a mixture of the heteropoly acids of molybdenum and of tungsten to form a blue, gel-like precursor, drying, and then calcining.

2. A process according to claim 1 wherein the hetero atoms of the heteropoly acids are one or both of phosphorus and silicon.

3. A process according to claim 1 wherein Y is P.

4. A process according to claim 1 wherein the catalyst has the formula $W_{4.8}Mo_{12}P_{1.4}Sb_{11.4}O_x$.

5. A process according to claim 1 wherein the catalyst has the formula $W_{4.8}Mo_{12}P_{1.4}Sb_{11.4}V_{1.1}Cs_{0.6}O_x$.

6. A process according to claim 1 wherein the catalyst is employed in the form of a solid shaped article.

* * * * *